United States Patent [19]

Sasai

[11] Patent Number: 4,928,699

[45] Date of Patent: May 29, 1990

[54] ULTRASONIC DIAGNOSIS DEVICE

[75] Inventor: Tsuguhisa Sasai, Tokyo, Japan

[73] Assignee: Olympus Optical Co., Ltd., Tokyo, Japan

[21] Appl. No.: 192,658

[22] Filed: May 11, 1988

[30] Foreign Application Priority Data

May 18, 1987 [JP] Japan .................................. 62-119026
May 18, 1987 [JP] Japan .................................. 62-119028
Jul. 29, 1987 [JP] Japan .................................. 62-187837

[51] Int. Cl.$^5$ .............................................. A61B 8/12
[52] U.S. Cl. .................................... 128/662.06; 128/4; 128/6
[58] Field of Search ............................ 128/662.06, 4–9

[56] References Cited

U.S. PATENT DOCUMENTS

| 4,374,525 | 2/1983 | Boba | 128/662.06 |
| 4,466,443 | 8/1984 | Utsugi | 128/662.06 |
| 4,466,444 | 8/1984 | Boba | 128/662.06 |
| 4,572,201 | 2/1986 | Kono et al. | 128/662.06 |
| 4,732,156 | 3/1988 | Nakamura | 128/662.06 X |

FOREIGN PATENT DOCUMENTS 133232 8/1983 Japan .............................. 128/662.06

Primary Examiner—Francis Jaworski
Attorney, Agent, or Firm—Stevens, Davis, Miller & Mosher

[57] ABSTRACT

An ultrasonic diagnosis device disclosed includes an endoscope with an ultrasonic diagnosis function, wherein an ultrasonic probe is arranged in the front end region of the portion to be inserted into a coelom or the like cavity, and is connected to an external rotational drive portion by a hollow multi-layered power transmission means to provide an observation field extending through the entire angular range. Signal wires from the probe and passed between outer and inner layers of the power transmission means which thus has a hollow center channel. Preferably, an observation optical system is arranged within the hollow channel to provide a visual field on the front side in the insertion direction, for a continuous confirmation purpose, permitting the insertion portion to be safely inserted even into a narrow cavity of an organ with a complex undulation.

15 Claims, 9 Drawing Sheets

FIG_1
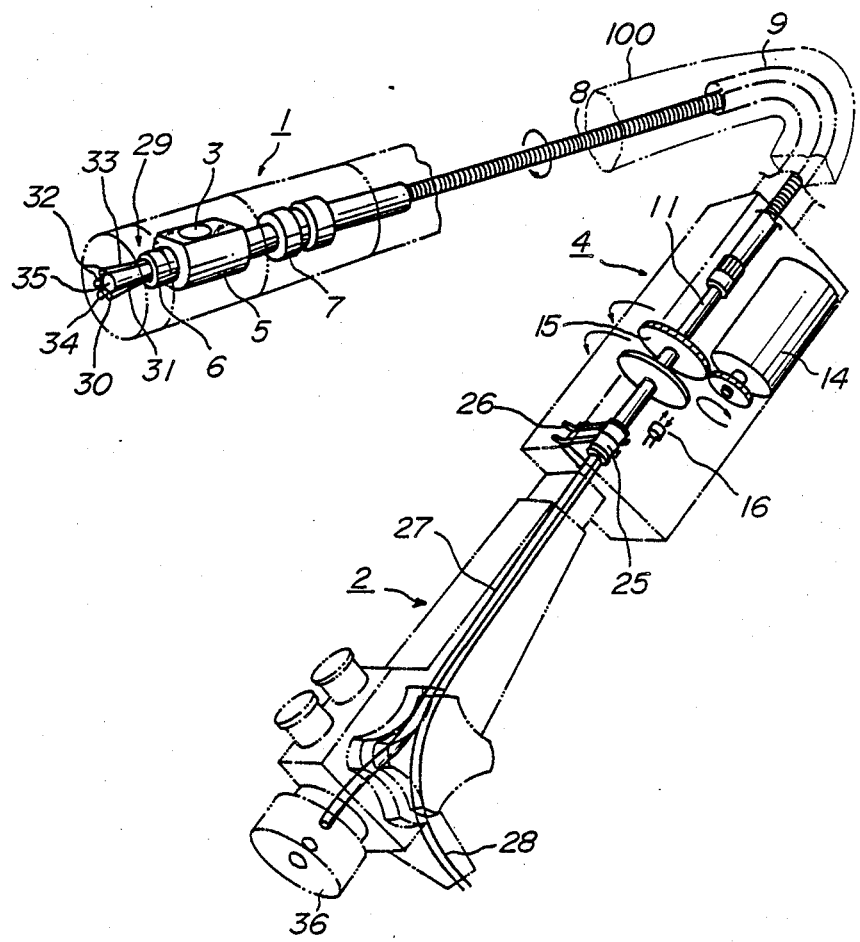

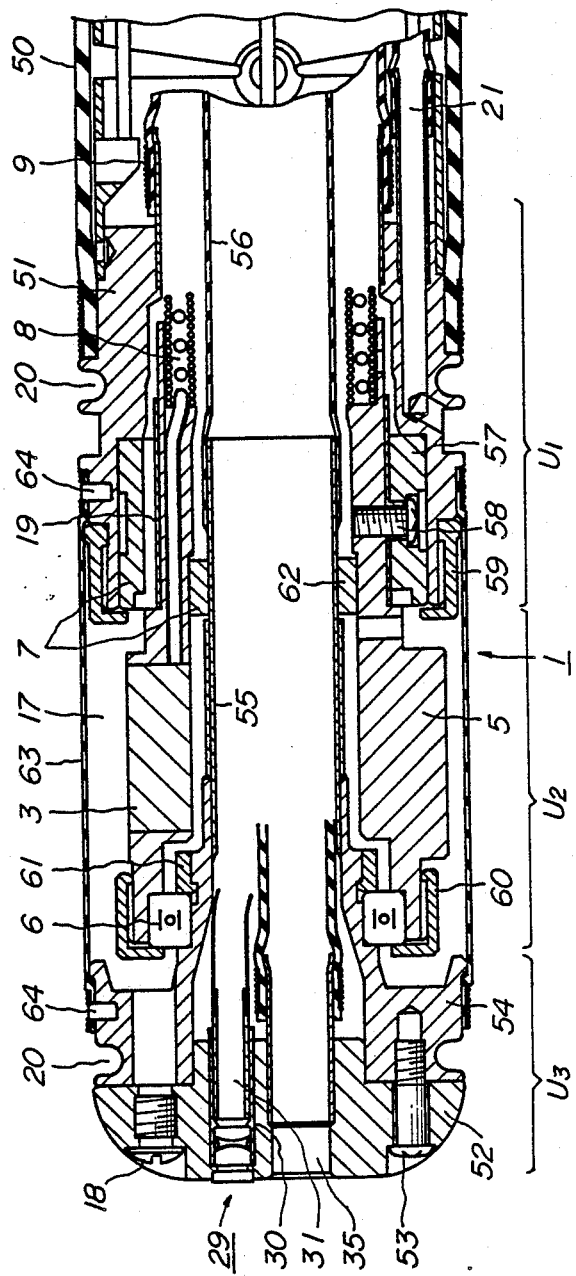

FIG_3
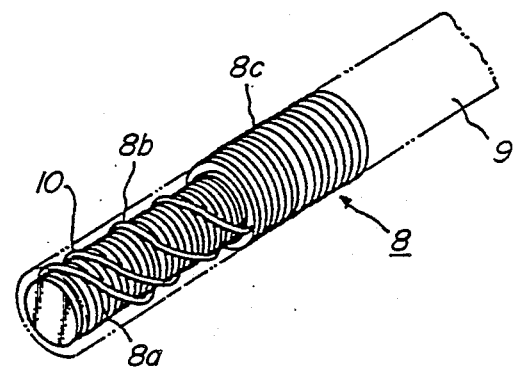
FIG_4
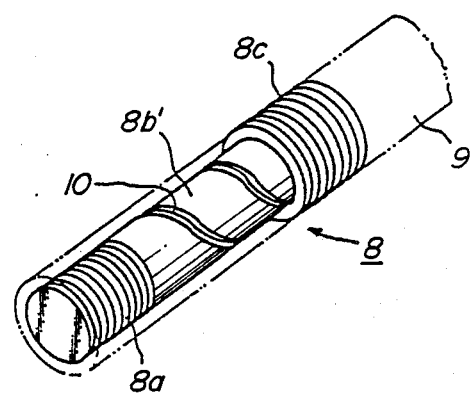

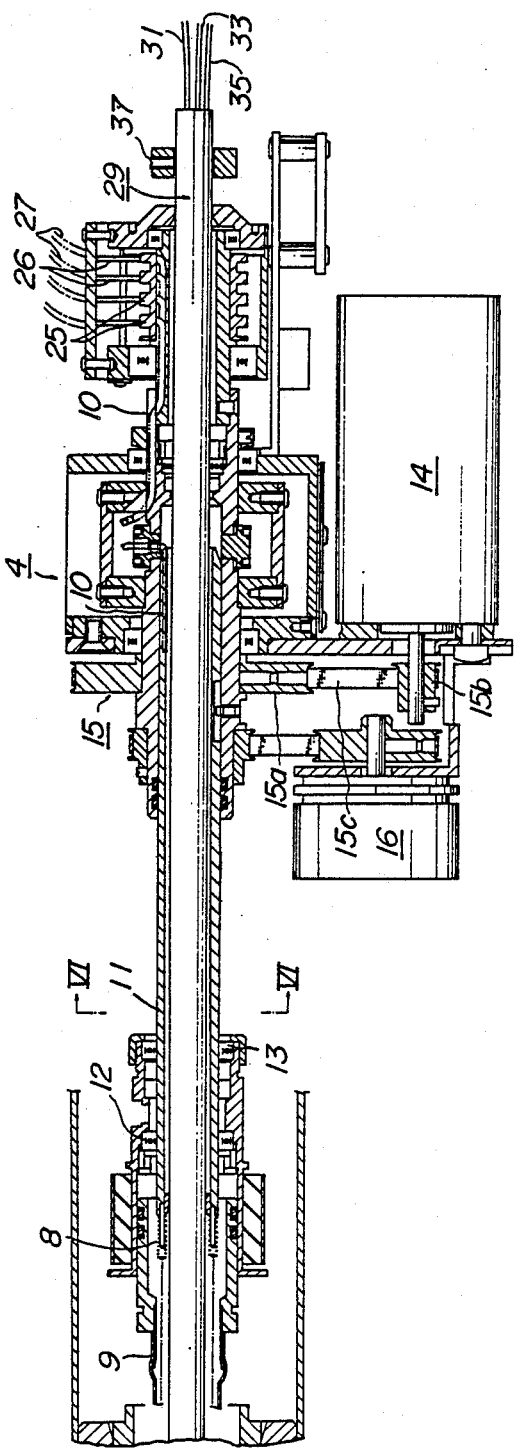

FIG_6
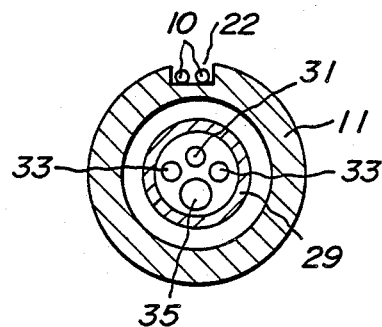
FIG_7
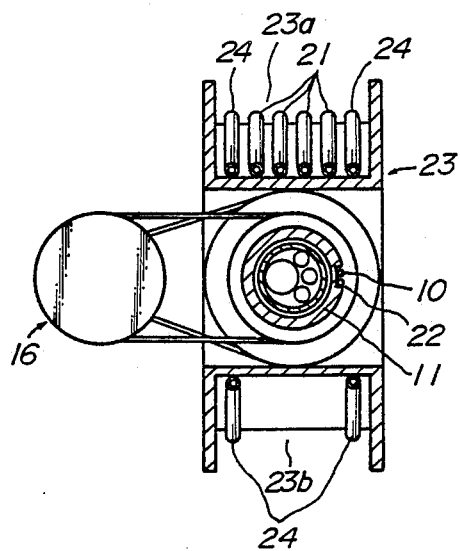

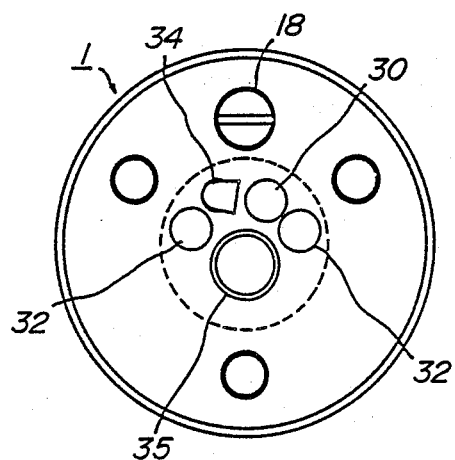
FIG_8

FIG_11

ULTRASONIC DIAGNOSIS DEVICE

BACKGROUND OF THE INVENTION

1. Field of the Invention

The present invention relates to an ultrasonic diagnosis device with an endoscope having an ultrasonic diagnosis function.

2. Description of the Related Art

Such an ultrasonic diagnosis device is known as being a combination of an endoscope with an ultrasonic scanning mechanism. Generally, an ultrasonic diagnosis device includes an insertion portion which is to be inserted into a coelom in the body of a human being, or the like cavity, and of which the front end region accommodates an ultrasonic probe so as to be rotatable about the center axis thereof. For causing the rotation of the probe, a drive means is formed of a motor and arranged in the drive portion outside of the cavity, while a power transmission means for drivably connecting the motor with the probe is formed of a hollow flexible shaft passed through the insertion portion. On the other hand, signal wires from the probe are passed through the interior space of the flexible shaft, and extend to an external ultrasonic observation device. Needless to say, ultrasonic scanning within the cavity is carried out by rotating the probe by means of the motor. Further provided is an optical observation system in which the optical image obtained by objective lens is guided to eyepiece lens by image guide fibers.

Conventionally, as the ultrasonic probe is arranged in the front end region of the insertion portion of the endoscope, and the flexible drive shaft occupies the center space of the insertion portion, the optical observation means has to be arranged on the side wall of the front end region. Hence, the direction of the visual field of the optical observation system is limited and has to extend transversely. The dead angle includes the direction in which the endoscope is to be inserted, so that it is difficult to manipulate the endoscope in the cavity. Particularly, when the known endoscope is to be used in the large intestine, or in the like organs with a complex undulation of the cavity, due to the difficulties in the manipulation arising from the limitation of the visual field, the insertion of the endoscope beyond the rectum is almost impossible, or accompanies a substantial risk even when possible.

An arrangement is known wherein the objective lens is arranged in the front end surface of the insertion portion of the endoscope, such that the direction in which the endoscope is to be inserted coincides with the optical visual field. Such an arrangement, however, suffers from the problem that the ultrasonic field is interrupted by the shadow of the optical observation means. It is thus impossible to obtain an ultrasonic field covering the entire angular range within a plane which is intersected perpendicularly by the axis of the front end of the endoscope, and practically obtainable field covers only the angular range of the order of 180°. As a result, in order to obtain a complete ultrasonic diagnosis image of the desired location within the coelom, it was necessary to carry out a complex and burdensome manipulation of the endoscope in the coelom, such as twisting or rotational movement.

SUMMARY OF THE INVENTION

The present invention has been conceived in view of the above-mentioned drawbacks of the prior art, and it is an object of the present invention to provide an ultrasonic diagnosis device which can be manipulated safely and easily even within a narrow cavity having a complex undulation, and which is capable of realizing a wide observation field of the ultrasonic diagnosis that covers at least substantially the entire angular range.

To this end, in accordance with the present invention, there is provided an ultrasonic diagnosis device comprising an ultrasonic probe arranged in a front end region of an insertion portion to be inserted into a cavity, such as a coelom of the body of a human being, the ultrasonic probe being rotatable about the center axis of the insertion portion, a drive means arranged in an external drive portion outside of the cavity, for causing the rotation of the ultrasonic probe, a hollow power transmission means passed through the insertion portion for drivably connecting the ultrasonic probe with the drive means, a hollow channel being so formed as to extend from the end surface of the front end region, through the interior of the power transmission means, and as far as a manipulation portion which serves to control operational functions of the front end region of the insertion portion.

An image transmission means may be arranged within the hollow channel, whereby an optical image can be obtained from a visual field on the front side of the device in the insertion direction of the front end region and the so-obtained image can be transmitted to the manipulation portion.

BRIEF DESCRIPTION OF THE DRAWINGS

FIG. 1 is a schematic view showing the overall arrangement of the ultrasonic diagnosis device according to one embodiment of the present invention;

FIG. 2 is a longitudinal-sectional view showing the arrangement of the front end region of the insertion portion thereof;

FIG. 3 is a perspective view showing one embodiment of the multi-layered hollow flexible shaft;

FIG. 4 is a perspective view showing another embodiment of the multi-layered hollow flexible shaft;

FIG. 5 is a longitudinal-sectional view showing the arrangement of the drive portion for the ultrasonic probe;

FIG. 6 is a cross-sectional view of the hollow shaft taken along the line VI—VI in FIG. 5;

FIG. 7 is a cross-sectional view of the drive portion shown in FIG. 5;

FIG. 8 is a front view showing the front end surface of the insertion portion according to the arrangement of FIG. 2;

DETAILED EXPLANATION OF THE PREFERRED EMBODIMENTS

Figure 9:
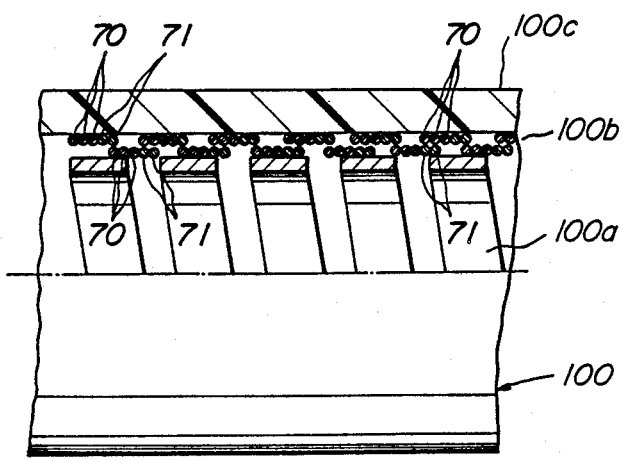
FIG. 9 is a partly broken side view showing one embodiment of the insertion portion in the device of FIG. 1.

The present invention will now be more fully explained with reference to some preferred embodiments shown in the drawings. There is schematically shown in FIG. 1 an ultrasonic diagnosis device according to the first embodiment of the present invention. The diagnosis device includes a flexible insertion portion 100 with a front end region 1 to be inserted into the cavity, and an external manipulation portion 2 for manipulating the front end region 1 from the outside of the cavity. An ultrasonic probe 3 for carrying out an ultrasonic diagnosis is arranged within the front end region 1, which is of a mechanical scanning type, or of a so-called mecha-radial type, and is thus rotatable about the longitudinal center axis of the front end region 1. A drive portion 4 for rotating the ultrasonic probe 3 is arranged adjacent to the manipulation portion 2, and is connected to the ultrasonic probe 3 through a power transmission means to be fully explained hereinafter. In accordance with the present invention, the ultrasonic probe 3, the drive portion 4 and the power transmission means arranged therebetween, each has a hollow structure such that a hollow channel extends therethrough, from the front end region of the insertion portion as far as the manipulation portion 2, in the vicinity of the center axis.

The ultrasonic probe 3 is of a conventional structure, including an ultrasonic vibration membrane made of PZT, lithium niobate, or other appropriate high polymer material, and a suitable damping material fixedly bonded thereto. As shown in FIG. 2, the ultrasonic probe 3 is secured to a support member 5 which is of a hollow cylindrical configuration, and is rotatably journaled by a ball bearing 6 and a journal bearing 7. The rear end of the support member 5 is integrally connected to the front end of a multi-layered hollow flexible shaft 8 forming part of the above-mentioned power transmission means. The flexible shaft 8 extends as far as the drive portion 4, and is rotatably arranged within a flexible tube 9 which, in turn, is passed through the insertion portion of the diagnosis device.

An ultrasonic diagnosis device with an ultrasonic probe of the mechanical scanning type, which is arranged within the front end region of the insertion portion and is connected to the motor in the drive portion by means of a flexible shaft, while signal wires from the ultrasonic probe are passed through the inner space of the flexible shaft, *per se*, is known and disclosed e.g. in Japanese Patent Application Laid-open Publication No. 57-190,552. In the present invention, however, the signal wires are guided along a different path, and the inner space of the flexible shaft is formed as a hollow channel which may serve to another purposes.

More particularly, in the embodiment as shown in FIG. 3, the flexible shaft 8 is of a three-layered structure including an inner coil layer 8a formed of a tightly wound wire material, an intermediate coil layer 8b formed of a loosely wound wire material which is relatively thick as compared with that of the inner layer 8a, and an outer coil layer 8c formed of a tightly wound wire material which is substantially of the same thickness as that of the inner layer 8a. Furthermore, the signal wires 10 from the ultrasonic probe 3, formed of an extremely fine coaxial cable, are helically arranged with an adequate slack within a space defined between the inner and outer layers 8a, 8c, and between the neighboring turns of the loosely wound wire material of the intermediate layer 8b. In order to positively avoid undesirable crush of the signal wires 10 between the inner and outer layers 8a, 8c, the wire material forming the intermediate layer 8b is greater in thickness than the signal wires 10.

Advantageously, the wire materials of the inner and outer layers 8a, 8c are wound in the same direction, while the wire material of the intermediate layer 8b is wound in the opposite direction. With such an arrangement, it is possible to realize a flexible shaft with smooth inner and outer surfaces, and with a minimized unevenness.

Furthermore, also in the embodiment shown in FIG. 4, the flexible shaft 8 is of a three-layered structure with the inner and outer coil layers 8a, 8c formed of tightly wound wire material, as in the embodiment of FIG. 3, and an intermediate layer 8b' which is formed of rubber or the like resilient material and is so arranged as to define a helical gap between the inner and outer layers. The signal wires 10 are arranged within the gap in the intermediate layer 8b' with an adequate slack, and the intermediate layer 8b' has a thickness which is greater than the diameter of the signal wires 10 in order to avoid the crush thereof.

In either of the embodiments of FIGS. 3 and 4, the signal wires 10 are completely protected between the inner and outer layers 8a, 8c of the flexible shaft 8, by means of the intermediate layer 8b, 8b', and arranged with an adequate slack. Thus, even when the insertion portion of the ultrasonic diagnosis device is subjected to a flexible deformation upon insertion into the cavity, the signal wires 10 are not subjected to tensile stress, and there is substantially no risk of breakdown of the signal wires. It is further possible to preserve within the flexible shaft 8, and throughout the entire length thereof, a hollow channel with a sufficient inner space which may serve to achieve required functions as will be fully explained hereinafter.

As shown in FIG. 5, the flexible shaft 8 with the above-mentioned structure is connected, on the rear end side of the insertion portion, to an ordinary hollow shaft 11 which is not flexible. The hollow shaft 11 is rotatably journaled by bearings 12, 13 arranged at appropriate locations within the drive portion 4, and connected to the drive motor 14 by a suitable coupling means 15. The coupling means 15, as shown in FIG. 5, may be formed of a drive belt coupling mechanism which includes a pulley 15a secured to the hollow shaft 11, a pulley 15b secured to the output shaft of the drive motor 14, and an endless belt 15c wrapped around, and extending between, the pulleys 15a, 15b. Alternatively, the coupling means 15 may be formed of a reduction gear train connected between the hollow shaft 11 and the output shaft of the drive motor 14.

With such an arrangement, by actuating the drive motor 14, the output torque of the motor is transmitted, through the coupling means 15, hollow shaft 11, flexible shaft 8 and hollow cylindrical support member 5, to the ultrasonic probe 3 at the front end region 1 of the insertion portion, to rotate the probe 3 by a desired angle about the center axis of the front end region 1. In order to make it possible to detect the direction in which the ultrasonic signal is sent from, and received by the probe, a rotary encoder 16 may be arranged in the drive portion 4 to detect such direction as the rotational angle of the hollow shaft 11 and to carry out a necessary signal processing in accordance with the detected angle.

As shown in FIG. 2, the front end region 1 of the insertion portion of the diagnosis device has an inner space in which the ultrasonic probe 3 is arranged, and which is further filled with a transmission medium for the ultrasonic wave, with an acoustic impedance which is substantially the same as that of the human body, such as liquid paraffin. The transmission medium is introduced from an opening in the front end surface of the insertion portion, which is normally sealed by a screw 18, completely through the inner space of the above-mentioned flexible tube 9, and up to a blind end (not shown) within the manipulation portion 2. In order to ensure that all the clearances on both inner and outer sides of the flexible shaft 8 are filled with the ultrasonic wave transmission medium, a plurality of longitudinal grooves 19 are formed e.g. on that side of the journal bearing 7 which is free from the sliding motion and is threadedly connected to the support member 5. The ultrasonic wave transmission medium on both inner and outer sides of the flexible shaft 8 serves to significantly reduce the frictional resistance to which the flexible shaft 8 is subjected during rotation thereof.

Furthermore, the front end region 1 of the insertion portion has an outer peripheral surface which is formed with a pair of circumferential grooves 20 for securing a known balloon (not shown). In order to ensure that deaerated water can be charged into, and discharged from the interior of the balloon when it is secured into the circumferential grooves 20, an inlet/outlet port is formed between the grooves 20 and connected, via a tube 21, with a corresponding mouthpiece (not shown) which is arranged on the side of the manipulation portion 2.

As mentioned previously with reference to FIGS. 3 and 4, the signal wires 10 from the ultrasonic probe 3 extend axially from the front end region 1 of the insertion portion to the drive portion 4, and radially between the inner and outer layers 8a, 8c of the flexible shaft 8. From the junction between the flexible shaft 8 and the hollow shaft 11, as shown in FIG. 6, the signal wires 10 are arranged in a longitudinal groove 22 formed in the outer peripheral surface of the hollow shaft 11. Furthermore, as shown in FIG. 7, longitudinal grooves 23a, 23b are also formed in the outer surfaces of a frame 23 for mounting various elements of the drive portion 4 thereon. The grooves 23a, 23b accommodate tubes 21 for the deaerated water, and control wires 24 for controlling the flexural motion of the flexible region which is arranged adjacent to the front end region 1 of the insertion portion. This frame 23 has been omitted in FIG. 5.

The signal wires 10, which are arranged in the longitudinal grooves 22 in the outer surface of the shaft 11, are connected to slip rings 25 on the rear side of the hollow shaft 11. The slip rings 25 are in sliding contact with contact elements 26, while signal wire 27 connected to these contact elements 26 are introduced into the manipulation portion 2, further passed through a so-called universal cord 28, and then connected to an ultrasonic observation means, not shown.

According to the present invention, as mentioned previously, all of the ultrasonic probe 3, the drive portion 4 therefor and the power transmission elements 8, 11 for connecting the probe with the drive portion, are of hollow structure such that a hollow channel extends from the front end region 1 of the insertion portion to the manipulation portion 2, along and adjacent to the center axis. An endoscope portion 29 is arranged in this hollow channel, such as to provide an optical visual field on the front side in the direction in which the insertion portion is inserted.

The endoscope portion 29, *per se,* is of a conventional arrangement including an observation lens assembly 30 and image guide fibers 31 for transmitting an optical image of the visual field, which lies on the front side in the insertion direction, toward the manipulation portion 2, an illumination lens assembly 32 and associated light guide fibers 33 for illuminating the visual field, a nozzle 34 for discharging flushing water or air when the surface of the observation lens assembly 30 is to be cleaned, and a channel element 35 for various purposes, e.g. for sucking out body liquid, or for passing a clamp or forceps when biopsy of a tissue is necessary. With such an arrangement of the endoscope portion 29, when the insertion portion is inserted into a coelom or the like cavity and the visual field is illuminated by the illumination lens assembly 32, it is possible to carry out an endoscopic observation with respect to the surface of a desired location where the diagnosis is to be effected through the observation lens assembly 30, by looking into the eyepiece lens 36 which is arranged at the manipulation portion 2.

The image guide fibers 31, light guide fibers 33 and channel element 35, all of which are passed through the above-mentioned support member 5 for the ultrasonic probe 3, flexible shaft 8 and hollow shaft 11, may be subjected to rotation jointly with the probe 3 as the latter is caused to rotate. Preferably, in order to prevent such a joint rotation, as shown in FIG. 5, the endoscope portion 29 cooperates with an appropriate lock means, such as a pin 37 arranged outside of the hollow shaft 11.

It will be appreciated from the foregoing description that the present invention provides a unique arrangement of the ultrasonic diagnosis device, wherein an ultrasonic probe 3 arranged in the front end region 1 of the insertion portion is secured to the hollow cylindrical support member 5 which itself is connected, by means of the hollow power transmission elements 8, 11, to the drive portion 4 for the probe 3. The resultant formation of a hollow channel, extending from the front end surface of the insertion portion up to the manipulation portion 2, makes it possible to accommodate the endoscope portion 29 providing a visual field on the front side of the insertion portrion in the direction in which the latter is to be inserted.

In order to readily and reliably realize such an arrangement, according to the illustrated embodiment of the present invention, the front end region 1 of the insertion portion may be divided into first, second and third units $U_1$, $U_2$ and $U_3$. More particularly, as shown in FIG. 2, the first unit $U_1$ is composed of an annular member 51 which is arranged adjacent to the flexible region 50. The second unit $U_2$ is formed of the hollow cylindrical support member 5 which supports the ultrasonic probe 3, and which is connected to the flexible shaft 8. The third unit $U_3$ includes a support member 52 in the form of a front end cap supporting the above-mentioned constitutional elements 30, 32 and 34 of the endoscope portion 29.

The front end region 1 divided into the first, second and third units $U_1$, $U_2$ and $U_3$ is assembled in the following manner.

First of all, a hard member 54 is integrally connected to the support member 52 of the third unit $U_3$ by a plurality of bolts 53. This hard member 54 has its rear end connected to a protective tube 55 and also to a flexible tube 56, both of which are adapted to protect the image fibers 31, light guide fibers 33 and channel element 35 of the endoscope portion 29.

In the next place, an annular bush 57 of the bearing 7, with an inner peripheral sliding surface, is fixedly connected to the rear end of the support member 5 in the second unit $U_2$, by radially extending bolts 58. The second unit $U_2$ is then inserted, from the rear side of the flexible shaft 8 into the first unit $U_1$, and is axially positioned by a threaded ring 59, with respect to the annular bush 57.

Subsequently, a threaded ring 60 is passed onto the third unit $U_3$ from the rear end side of the flexible tube 56, and the ball bearing 6 is axially secured to the hard member 54 by another threaded ring 61. An annular bearing member 62 of the bearing 7, with an outer peripheral sliding surface, is passed onto the protective tube 55. The third unit $U_3$ is then inserted into the hollow cylindrical support member 5 and the flexible shaft 8 of the second unit $U_2$, from the rear end side of the third unit, and the ball bearing 6 is axially positioned by the threaded ring 60, with respect to the second unit $U_2$.

Finally, the first and third units $U_1$, $U_3$ are bridged by a cylindrical member 63 having a sufficient torsional rigidity and formed of a synthetic resin material, such as polyethylene, and the relative angular position of the two units are fixed by knock pins 64. The cylindrical member 63 on its both ends are adhered to the corresponding units $U_1$, $U_3$, and the knock pins 64 are also adhered to the corresponding units.

When, as in the above-mentioned embodiment, the front end region 1 of the insertion portion is divided into the first, second and third units $U_1$, $U_2$ and $U_3$, it is thus possible to sequentially assemble the front end region 1 by inserting the second unit $U_2$ into the first unit $U_1$, and thereafter inserting the third unit $U_3$ into the second unit $U_2$. In other words, the front end region 1 with a unique internal arrangement can be readily assembled in a reliable manner.

It is of course that the ultrasonic wave transmission medium as mentioned hereinbefore is filled within the annular space between the first and second units $U_1$, $U_2$ and also within the annular space between the second and third units $U_2$, $U_3$, so as to reduce the frictional resistance to which the flexible shaft 8 of the second unit $U_2$ is subjected as it is placed into rotation relative to the first and third units $U_1$, $U_3$.

FIG. 9 shows the detailed arrangement of one embodiment of the insertion portion. The insertion portion 100, which extends from the flexible region 50 to the drive portion 4, is of a three layered structure including an inner layer 100a, an intermediate braided layer 100b covering the inner layer 100a, and an outer layer 100c covering the braided layer 100b. The inner layer 100a is an annular element formed by helically winding resilient metal strip. The braided layer 100b is formed by braiding extremely fine metal wires 70 and extremely fine high strength fibers 71 into a tubular mesh body. The metal wires 70 may consist of stainless wires having the diameter of approximately 0.02–0.15 mm, while the high strength fibers may consist of polyimide fibers with the diameter of approximately 0.02 mm or less, such as alamide fiber HM-50, the product of Teijin Co., Ltd., Japan. Further, the outer layer 100c is in the form of a resilient sheath made of a flexible synthetic resin material. With such an arrangement, the thickness of the braided layer 100b can be reduced to approximately 0.12 mm or less, to thereby minimize the outer diameter of the insertion portion 100.

The above-mentioned high strength fibers 71 included in the intermediate braided layer 100b of the insertion portion 100 has a high heat durability capable of withstanding the temperature of 200° C. continuously, and 400° C. at the maximum, a tensile strength of 310 kg/mm² which is higher than that of stainless steels, as well as a twisting property which is superior than conventional polyimide fibers, such as "Kevlar" fibers produced by DuPont, U.S.A., and permits a very fine twisting of the fibers 71. The high strength fibers 71 formed of extremely fine polyimide fibers, when they are twisted very finely, serve to effectively suppress the recovery of the twisting, and make it possible to realize the intermediate braided layer which is excellent in straightness and appearance. It is of course that the thickness of the intermediate braided layer 100b can be adjusted by increasing or decreasing the number of the high strength fibers 71 which are twisted together.

Figure 10:
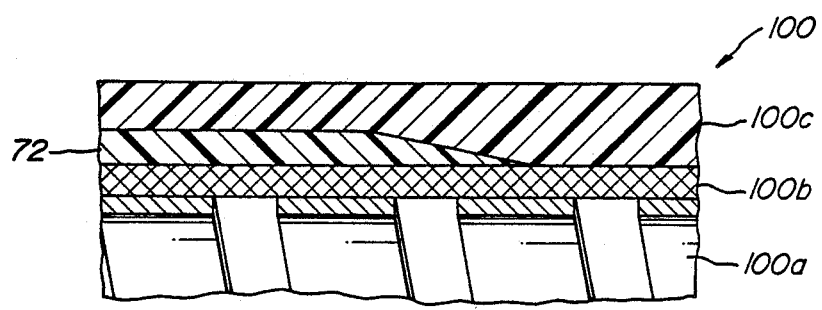
FIG. 10 is a partly broken side view showing another embodiment of the insertion portion along the region where the flexural rigidity changes gradually.

FIG. 10 shows the detailed arrangement of still another embodiment of the insertion portion 100. In this case also, the insertion portion 100 is of a three layered structure including an inner layer 100a, an intermediate braided layer 100b covering the inner layer 100a, and an outer layer 100c covering the braided layer 100b. The inner layer 100a and the braided layer 100b are similar to those in the embodiment of FIG. 9. The insertion portion 100 extends between the flexible region 50 and the drive portion 4, and has an end region adjacent to the drive portion 4, where a tubular element 72 composed of hard resin material is arranged radially between the braided layer 100b and the outer layer 100c. The tubular element 72 has a thickness which gradually increases away from the drive portion 4, to thereby provide a gradually decreasing flexural rigidity. Correspondingly to the above, the outer layer 100c, which is formed of a relatively soft resin material as compared with the tubular element 72, has a thickness which gradually decreases toward the drive portion 4, and an outer diameter which is substantially constant throughout the entire length of the insertion portion 100. With such an arrangement, it is possible to avoid an abrupt or discontinuous change in the flexural rigidity of the insertion portion 100 near the junction between that portion 100 and the drive portion 4. Hence, it is possible to bend the insertion portion 100 with a smoothly variable curvature, and to improve the durability of the insertion portion 100.

Figure 11:
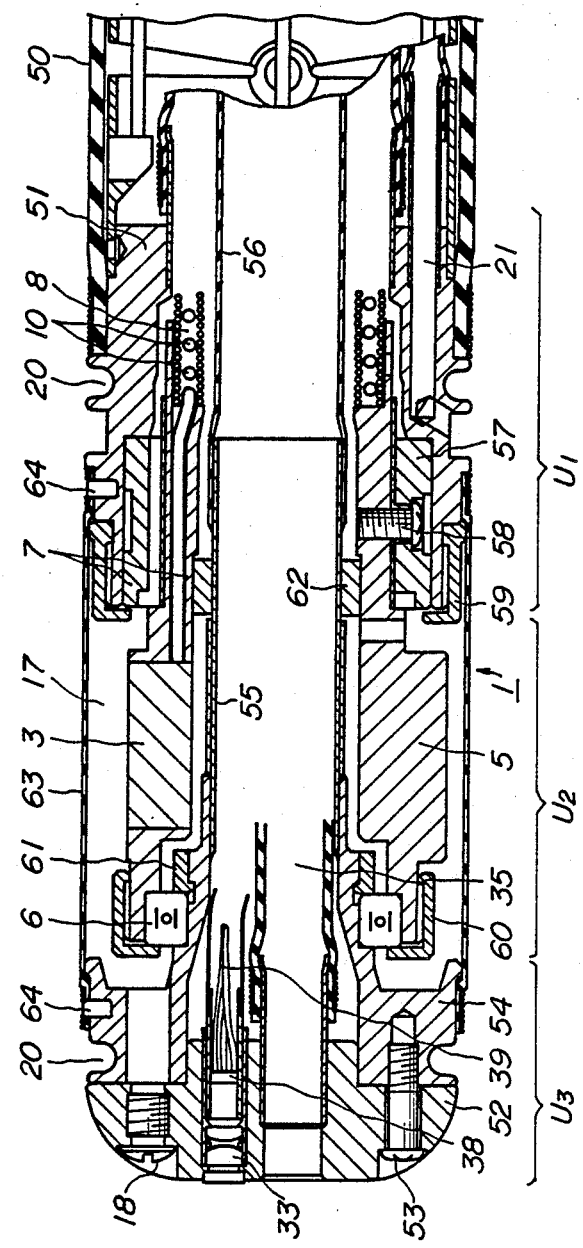
FIG. 11 is a longitudinal-sectional view similar to FIG. 2, but showing another embodiment of the endoscope optical system.
Figure 12:
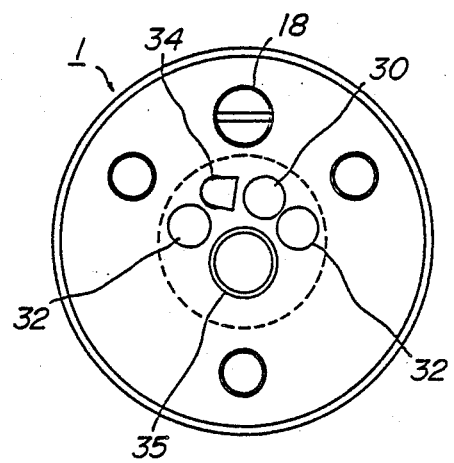
FIG. 12 is a front view similar to FIG. 8, but showing the front end surface of the insertion portion according to the arrangement of FIG. 11.

FIGS. 11 and 12 show another embodiment of the endoscope portion 29 which is inserted into the hollow channel mentioned above. In this embodiment also, the front end region 1 of the insertion portion is divided into the first, second and third units $U_1$, $U_2$ and $U_3$. This embodiment is essentially the same as the previous one, except that means for transmitting the optical image in the visual field on the front side in the insertion direction includes a lens assembly 30, a solid state imaging device 38, such as a charge coupled device (CCD), and associated electric signal wires 39.

According to the present invention, as mentioned above, a hollow channel is formed so as to extend from the front end region 1 of the insertion portion up to the manipulation portion 2 along the center axis, and the hollow channel may serve to accommodate the endoscope portion 29 which makes it is possible to directly obtain the optical image on the front side of the diagnosis device in its insertion direction. All the embodiments with such an endoscope optical system are thus free from limitations in the direction of the visual field, and it is possible to insert the diagnosis device even into narrow coelom of large intestine or the like organs with a complex undulation, up to the desired location, with a remarkably improved safety which can be achieved by continuously observing the front side of the device in the insertion direction. Moreover, the ultrasonic probe 3 can be rotated into any angular position, by 360° if necessary, so that it is possible to obtain a complete ultrasonic diagnosis image of the desired location easily and positively, without requiring any difficult and complex manipulation.

What is claimed is:

1. An ultrasonic diagnosis device comprising an ultrasonic probe arranged in a front end region of an insertion portion to be inserted into a cavity, the ultrasonic probe being supported by a hollow cylindrical member which is rotatable about a center axis of the insertion portion, a drive means arranged in an external drive portion located outside of the cavity, for causing the rotation of the ultrasonic probe, a hollow power transmission means which passes through the insertion portion, for drivably connecting said hollow cylindrical member with said drive means, a hollow channel extending from an end surface of the front end region, through said hollow cylindrical member and an interior of said hollow power transmission means to a manipulation portion located outside the cavity which controls operational functions of the front end region of the insertion portion, and an image transmission means arranged within said hollow channel, for obtaining an optical image for a visual field on the front side of the device in the insertion direction of the front end region and for transmitting said optical image to the manipulation portion.

2. The diagnosis device as claimed in claim 1, further comprising an observation lens assembly arranged in the end surface of said front end region of the insertion portion, wherein said image transmission means includes image guide fibers arranged behind said lens assembly which pass through said hollow channel.

3. The diagnosis device as claimed in claim 1, further comprising a solid state imaging device arranged in the end surface of said front end region of the insertion portion, wherein said image transmission means includes electric signal wires connected to said imaging device which pass through said hollow channel.

4. The diagnosis device as claimed in claim 1, wherein said hollow channel is adapted to accommodate therein a channel element allowing passage therethrough of a fluid and/or an elongate medical instrument.

5. The diagnosis device as claimed in claim 1, wherein said hollow power transmission means includes a multilayered structural body with at least an outer layer and an inner layer, both of which are formed of resilient material, and wherein signal wires extending from said ultrasonic probe to said manipulation portion are passed between the outer and inner layers.

6. The diagnosis device as claimed in claim 5, wherein said hollow power transmission means includes an inner layer and an outer layer, each formed of a coil of tightly wound wire material, and an intermediate layer formed of a coil of loosely wound wire material which is greater than said signal wires in thickness, and said signal wires are helically arranged, with a slack, in a space between neighboring turns of the coil of said intermediate layer.

7. The diagnosis device as claimed in claim 6, wherein the wire materials of the coils of the inner and outer layers are helically wound in one direction, while the wire material of the coil of the intermediate layer is would in the opposite direction.

8. The diagnosis device as claimed in claim 1, wherein said front end region includes first, second and third units, said first unit including an annular member arranged adjacent to a flexible region of said insertion portion, said second unit including said hollow cylindrical member and having a rear section which is connected to said power transmission means and is rotatably supported in said first unit, with a bearing therebetween and also having a front section which is arranged axially in front of the first unit and which supports said ultrasonic probe, said third unit including a support member with a front section which is arranged axially in front of said second unit and which supports an optical system for obtaining an optical image from a visual field on the front side in the direction in which said insertion portion is inserted, the support member of the third unit being arranged in, and relatively rotatably supporting said front section of the second unit, with a bearing therebetween.

9. The diagnosis device as claimed in claim 8, wherein an ultrasonic wave transmission medium is filled within an annular space defined between said first and second units, and also within an annular space defined between said second and third units, said transmission medium having an acoustic impedance which is substantially the same as that of a human body.

10. An ultrasonic diagnosis device comprising an ultrasonic probe arranged in a front end region of an insertion portion to be inserted into a cavity, the ultrasonic probe being supported by a hollow cylindrical member which is rotatable about a center axis of the insertion portion, a drive means arranged in an external drive portion located outside of the cavity, for causing the rotation of the ultrasonic probe, a hollow power transmission means which passes through the insertion portion, for drivably connecting said hollow cylindrical member with said drive means, a hollow channel extending from an end surface of the front end region, through said hollow cylindrical member and an interior of said hollow power transmission means to a manipulation portion located outside the cavity which controls operational functions of the front end region of the insertion portion, said hollow power transmission means including a multilayered structural body with at least an outer layer and an inner layer, both of which are formed of resilient material, and signal wires extending from said ultrasonic probe to said manipulation portion and passing between said outer and inner layers.

11. The diagnosis device as claimed in claim 10, wherein said hollow channel is adapted to accommodate therein a channel element allowing passage therethrough of a fluid and/or an elongate medical instrument.

12. The diagnosis device as claimed in claim 10, wherein said hollow power transmission means includes an inner layer and an outer layer, each formed of a coil of tightly wound wire material, and an intermediate layer formed of a coil of loosely wound wire material which is greater than said signal wires in thickness, and said signal wires are helically arranged, with a slack, in a space between neighboring turns of the coil of said intermediate layer.

13. The diagnosis device as claimed in claim 12, wherein the wire materials of the coils of the inner and outer layers are helically wound in one direction, while the wire material of the coil of the intermediate layer is wound in the opposite direction.

14. The diagnosis device as claimed in claim 15, wherein an ultrasonic wave transmission medium is filled within an annular space defined between said first and second units, and also within an annular space defined between said second and third units, said transmission medium having an acoustic impedance which is substantially the same as that of a human body.

15. An ultrasonic diagnosis device comprising an ultrasonic probe arranged in a front end region of an insertion portion to be inserted into a cavity, the ultrasonic probe being supported by a hollow cylindrical member which is rotatable about a center axis of the insertion portion, a drive means arranged in an external drive portion located outside of the cavity, for causing the rotation of the ultrasonic probe, a hollow power transmission means which passes through the insertion portion, for drivably connecting said hollow cylindrical member with said drive means, and a hollow channel extending from an end surface of the front end region, through said hollow cylindrical member and an interior of said hollow power transmission means to a manipulation portion located outside the cavity which controls operational functions of the front end region of the insertion portion, said front end region including first, second and third units, said first unit including an annular member arranged adjacent to a flexible region of said insertion portion, said second unit including said hollow cylindrical member and having a rear section which is connected to said power transmission means and is rotatably supported in said first unit, with a bearing therebetween, and also having a front section which is arranged axially in front of the first unit and which supports said ultrasonic probe, said third unit including a support member with a front section which is arranged axially in front of said second unit and which supports an optical system for obtaining an optical image from a visual field on the front side in the direction in which said insertion portion is inserted, the support member of the third unit being arranged in, and relatively rotatably supporting said front section of the second unit, with a bearing therebetween.

* * * * *